(12) United States Patent
Walker et al.

(10) Patent No.: US 8,641,682 B2
(45) Date of Patent: Feb. 4, 2014

(54) APPLICATOR

(75) Inventors: Rodney G. Walker, Hamilton (NZ); Todd D. Ebbett, Hamilton (NZ); Colin A. Standing, Hamilton (NZ)

(73) Assignee: Simcro Tech Ltd., Frankton, Hamilton (NZ)

( * ) Notice: Subject to any disclaimer, the term of this patent is extended or adjusted under 35 U.S.C. 154(b) by 895 days.

(21) Appl. No.: 12/451,566

(22) PCT Filed: May 21, 2008

(86) PCT No.: PCT/NZ2008/000113
§ 371 (c)(1),
(2), (4) Date: Feb. 2, 2010

(87) PCT Pub. No.: WO2008/143529
PCT Pub. Date: Nov. 27, 2008

(65) Prior Publication Data
US 2010/0145283 A1    Jun. 10, 2010

(30) Foreign Application Priority Data
May 21, 2007 (NZ) ........................................ 555327

(51) Int. Cl.
*A61M 5/00* (2006.01)
*A61M 5/32* (2006.01)

(52) U.S. Cl.
USPC ............ 604/207; 604/198; 604/192; 604/208

(58) Field of Classification Search
USPC ......... 604/208, 211, 207, 192, 187, 210, 198, 604/209
See application file for complete search history.

(56) References Cited

U.S. PATENT DOCUMENTS

| 3,261,243 | A | 7/1966 | Ellison |
| 3,905,365 | A | 9/1975 | Columbo |
| 4,142,654 | A | 3/1979 | Doubleday et al. |
| 4,695,274 | A | 9/1987 | Fox |

(Continued)

FOREIGN PATENT DOCUMENTS

| JP | 2001170090 | 6/2001 |
| WO | 2005030290 | 4/2005 |

OTHER PUBLICATIONS

English Abstract of JP2001170090.

*Primary Examiner* — Emily Schmidt
*Assistant Examiner* — Bradley G Thomas, Jr.
(74) *Attorney, Agent, or Firm* — Dykema Gossett PLLC

(57) ABSTRACT

An applicator, for example an injector (100), includes a flow control means including a first member (2) and a second member (6) for controlling flow from an inlet (4) to an outlet (5). A hinged linkage (17) is provided having a first end (18) rotatably engaged with the first member and a second end (19) rotatably engaged with the second member. The linkage (17) is moveable between a collapsed position and an over-center locked position which prevents relative movement of the first member (2) towards the second member (6). Linkage unlocking means (28) are provided which move the hinge (22) away from the over-center locked position so that the first and second members can be moved together.
A similar linkage (10) prevents unwanted movement of a needle shroud (8).
A needle shroud (8) which can be used to remove the needle (7) from the injector (100) is also described.

18 Claims, 6 Drawing Sheets

(56) References Cited

U.S. PATENT DOCUMENTS

| | | |
|---|---|---|
| 4,772,272 A | 9/1988 | McFarland |
| 4,850,996 A | 7/1989 | Cree |
| 4,911,693 A | 3/1990 | Paris |
| 4,946,446 A | 8/1990 | Vadher |
| 5,049,136 A | 9/1991 | Johnson |
| 5,951,516 A | 9/1999 | Bunyan |
| 6,460,787 B1 | 10/2002 | Hartle et al. |
| 7,699,813 B2 | 4/2010 | Liversidge |
| 2005/0137575 A1* | 6/2005 | Thompson et al. ........... 604/522 |
| 2007/0084899 A1 | 4/2007 | Taylor |

* cited by examiner

APPLICATOR

The present invention relates to applicators, and in particular, but not exclusively, to applicators of the type used to inject remedies into animals.

BACKGROUND OF THE INVENTION

In order to optimise yield from farmed animals, in particular pigs and cattle, a number of remedies may be injected into the animal.

The term "remedy" is used herein to include any drug, medicine, remedy, or therapeutic preparation, when in a form suitable for dispensing from an applicator, or more specifically an injector, as the context requires.

Injection of the animal can be difficult, and there exists a danger that the user of the injector may be accidentally jabbed with the needle. Accidents of this type are known as "needle stick".

In extreme cases the user may even receive an accidental dose or partial dose of the remedy. This is particularly undesirable, as some of the remedies used with this type of applicator may have significant adverse effects on the health and wellbeing of a human being.

Some injectors of the prior art attempt to reduce the risk of accidental needle stick by covering the needle of the injector with a retractable shroud. The shroud may be spring loaded so that it retracts automatically as the needle is inserted into the animal.

An additional level of safety is provided by injectors such as that described in U.S. Pat. No. 5,951,516, which discloses an applicator with a needle shroud and a trigger which must be depressed to an intermediate position before the shroud can be retracted. A trigger lock provided on the body of the injector prevents the trigger from being moved to an operational position until the shroud has been retracted by a desired amount, corresponding to a desired penetration of the needle into the animal. Only when this has occurred can the trigger be moved to the operational position and the dose injected.

The injector described in U.S. Pat. No. 5,951,516 is powered by a pressurised gas such as a compressed air or liquid petroleum gas. It would be desirable to develop an injector which had a high level of safety but which did not depend on a pressurised gas as a power source. It would also be advantageous if the safety mechanism did not depend on any sharp edge abutment, as these may be prone to wear.

Other types of applicator may also benefit from a simple and reliable mechanism which prevents doses of fluid from being dispensed accidentally, as this can cause waste of expensive product. In addition, even if a blunt application means such as a nozzle is used, it may still be desirable to shield the application means with a moveable shroud, for example if the application means is particularly delicate and easily damaged.

With injectors, a further potential source of danger to the user is the process of replacing the needle. The needle has a threaded portion with engages a complementary threaded portion provided on the outlet of the injector. The needle is provided with a formation with which a suitable tool, such as a spanner, can be engaged in order to rotate the needle and thereby engage or disengage the needle with the outlet.

The injectors of the prior art may require the needle shroud, if provided, to be retracted or removed during this process, leaving the sharp end of the needle exposed.

OBJECT OF THE INVENTION

It is an object of the present invention to provide an applicator which will overcome or ameliorate problems with applicators of the prior art.

It is an alternative object of the present invention to provide an injector which will overcome or ameliorate problems with injectors of the prior art.

It is a further alternative object to provide a needle shroud for an injector which will overcome or ameliorate problems with injector shrouds of the prior art.

It is a further alternative object to provide a useful choice.

Other objects of the present invention may become apparent from the following description, which is given by way of example only.

SUMMARY OF THE INVENTION

According to one aspect of the present invention there is provided an applicator including;
  an inlet for receiving a fluid to be dispensed;
  an outlet for dispensing the fluid to be dispensed;
  flow control means for controlling flow from the inlet to the outlet, the flow control means including a first member and a second member, the arrangement being such that relative movement of the first member towards the second member causes fluid to flow from the outlet;
  a hinged linkage having a first end rotatably engaged with the first member, a second end rotatably engaged with the second member, and a hinge intermediate the first and second ends, the linkage moveable between a collapsed position wherein the hinge is on a first side of a notional axis extending between first and second ends, and an over-centre locked position wherein the hinge is on an opposite side of the notional axis between the first and second ends and the hinged linkage prevents relative movement of the first member towards the second member;
  linkage unlocking means operable to move the hinge from the over-centre locked position to the first side of the notional axis between the first and second ends, so that the hinged linkage can be moved to the collapsed position as the first and second members are moved together.

Preferably the linkage is biased towards the over-centre locked position.

Preferably the linkage unlocking means includes a trigger.

Preferably at least one of the connections between the ends of the hinged linkage and the first and second members allows relative movement between the linkage and the respective member in addition to the rotational movement.

Preferably the relative movement includes slideable movement between the respective member and the end of the hinged linkage.

Preferably at least one of the connections between the ends of the hinged linkage and the first and second members includes a pin slideably engaged with a slot.

Preferably the applicator is suitable for applying an animal remedy to an animal.

Preferably the first and second members are handles.

Preferably the applicator is an injector.

According to a second aspect of the present invention there is provided an applicator including;
  a body provided with a first handle;
  an inlet for receiving a remedy to be dispensed;
  an outlet for dispensing the remedy, the outlet provided with application means connection means for connecting an application means to the outlet;
  flow control means for controlling flow of the remedy from the inlet to the outlet;
  a shroud connected to the body and moveable between an extended position wherein the shroud covers an application means attached in use to the application means connection means, and a retracted position wherein a required length of the application means protrudes from the shroud;

a first hinged linkage having a first end rotatably engaged with the shroud, a second end rotatably engaged with the first handle, and a hinge intermediate the first and second ends, the first hinged linkage moveable between a collapsed position wherein the hinge is on a first side of a notional axis extending between the first and second ends, and an over-centre locked position wherein the hinge is on an opposite side of the notional axis between the first and second ends, the arrangement being such that the hinged linkage prevents the shroud from moving from the extended position when in the over-centre locked position;

biasing means to bias the first hinged linkage towards the over-centre locked position; and linkage unlocking means operable to move the hinge from the over-centre locked position to the first side of the notional axis between the first and second ends, so that the linkage can be moved to the collapsed position as the shroud is moved to the retracted position.

Preferably the flow control means includes a second handle, wherein relative movement of the second handle towards the first handle causes the remedy to flow from the outlet, and the applicator includes a second hinged linkage having a first end rotatably engaged with the first handle, a second end rotatably engaged with the second handle, and a hinge intermediate the first and second ends, the second linkage moveable between a collapsed position wherein the hinge is on a first side of a notional axis extending between first and second ends, and an over-centre locked position wherein the hinge is on an opposite side of the notional axis between the first and second ends and the second hinged linkage prevents relative movement of the second handle towards the first handle, the arrangement being such that movement of the first hinged linkage to the collapsed position causes the hinge of the second hinged linkage to move from the over-centre locked position to the first side of the notional axis between the first and second ends of the second hinged linkage, so that the second hinged linkage can be moved to the collapsed position as the first and second handles are moved together.

Preferably at least one of the connections between the ends of the second hinged linkage and the handles allows relative movement between the linkage and the respective handle in addition to the rotational movement.

Preferably the relative movement includes slideable movement between the end of the second hinged linkage and the respective handle.

Preferably at least one of the connections between the ends of the second hinged linkage and the handles includes a pin slideably engaged with a slot.

Preferably the body is connected to a first end of the first handle.

Preferably the second handle is rotatably connected to the first handle at a distal end to the body.

Preferably the shroud is biased towards the extended position.

Preferably the applicator is an injector and the application means is a needle.

Preferably the shroud is detachable from the injector and is operable in a second mode of operation as a means for removing the needle from the injector, the shroud including a body provided with a cavity shaped and dimensioned to receive the needle when in use in the second mode of operation, the cavity including a formation adapted to engage a complementary formation of the needle so that rotation of the needle shroud causes rotation of the needle, thereby allowing disengagement of the needle from the injector with the needle housed in the cavity.

According to a third aspect of the present invention there is provided an applicator including;

a body provided with a first handle;

an inlet for receiving a fluid to be dispensed;

an outlet for dispensing the fluid to be dispensed;

a second handle, wherein relative movement of the second handle towards the first handle causes fluid to flow from the outlet;

a hinged linkage having a first end rotatably engaged with the first handle, a second end rotatably engaged with the second handle, and a hinge intermediate the first and second ends, the linkage moveable between a collapsed position wherein the hinge is on a first side of a notional axis extending between the first and second ends, and an over-centre locked position wherein the hinge is on an opposite side of the notional axis between the first and second ends and the hinged linkage prevents relative movement of the second handle towards the first handle;

linkage unlocking means operable to move the hinge from the over-centre locked position to the first side of the notional axis between the first and second ends, so that the hinged linkage can be moved to the collapsed position as the first and second handles are moved together.

Preferably the applicator is suitable for applying an animal remedy to an animal.

According to a fourth aspect of the present invention there is provided a needle shroud for an injector including a body provided with connecting means for releasable connection to the injector when in a first mode of operation, the body having an aperture therethrough shaped and dimensioned to allow a needle to extend through the body when the needle shroud is connected to the injector, the body of the needle shroud provided with a cavity shaped and dimensioned to receive the needle when in use in a second mode of operation, the cavity including a formation shaped and dimensioned to be engageable with a complementary formation of the needle when the needle has been received in the cavity, so that rotation of the needle shroud causes rotation of the needle, thereby allowing disengagement of the needle from the injector with the needle housed in the cavity.

According to a further aspect of the present invention there is provided an injector substantially as herein described with reference to the accompanying drawings.

According to a still further aspect of the present invention there is provided a needle shroud substantially as herein described with reference to FIGS. 1 to 4 and FIG. 6.

Further aspects of the invention, which should be considered in all its novel aspects, will become apparent from the following description given by way of example of possible embodiments of the invention.

BRIEF DESCRIPTION OF THE FIGURES

FIG. 1A Is a diagrammatic end view of the needle shroud of the injector of FIG. 1.

BEST MODES FOR PERFORMING THE INVENTION

Figure 1:
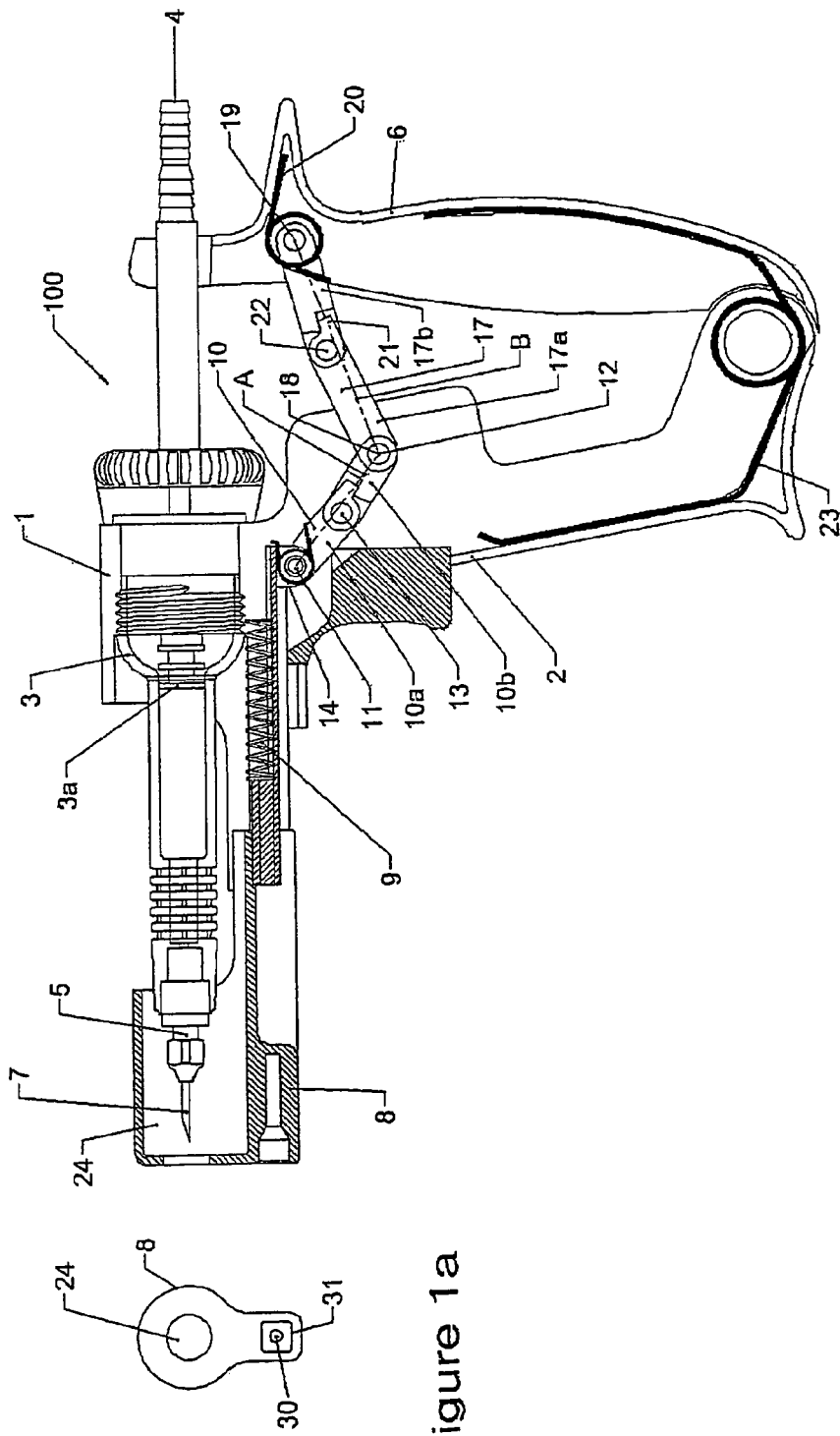
FIG. 1 Is a diagrammatic cross-section side view of an applicator of the present invention configured as an injector, with the first and second linkages in their over-centre locked positions and the needle shroud in an extended position.

Referring first to FIG. 1, an applicator is shown according to one embodiment of the present invention. The applicator is configured as an injector, generally referenced 100.

The injector 100 has a body 1 which is provided with a first handle 2. The handle 2 is typically formed as an integral component with the body 1. The body is provided with a cylinder or barrel 3 within which a plunger 3a is reciprocable in order to move fluid from an inlet 4 to an outlet 5 of the injector 100. The plunger is actuated by relative movement of the first handle 2 towards the second handle 6, which causes a remedy in the barrel 3 to move through the outlet 5 and hence through a needle 7 which is attached to the outlet 5.

Figure 3:
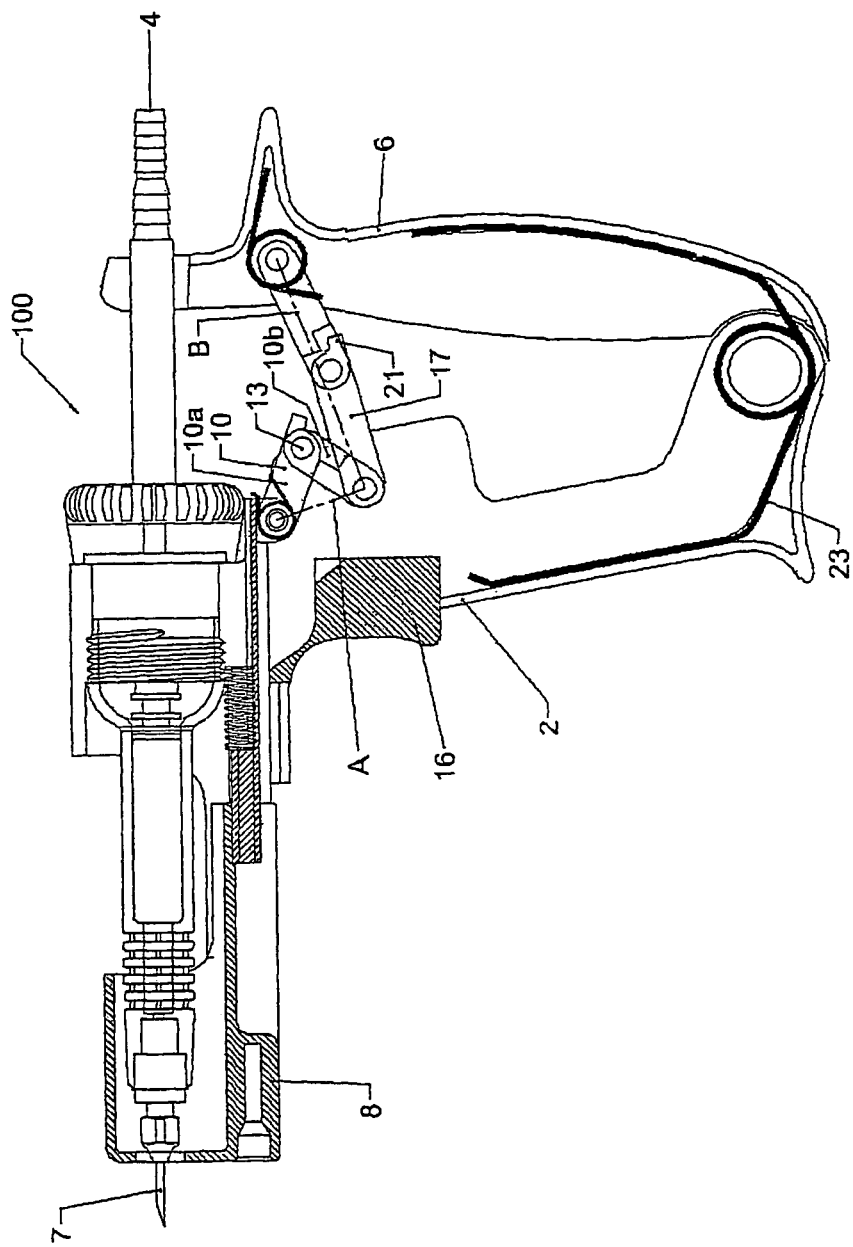
FIG. 3 Is a diagrammatic cross-section side view of the injector of FIG. 1, with the first linkage in a collapsed position, the needle shroud in the retracted position and the second linkage moved away from the over-centre locked position.
Figure 4:
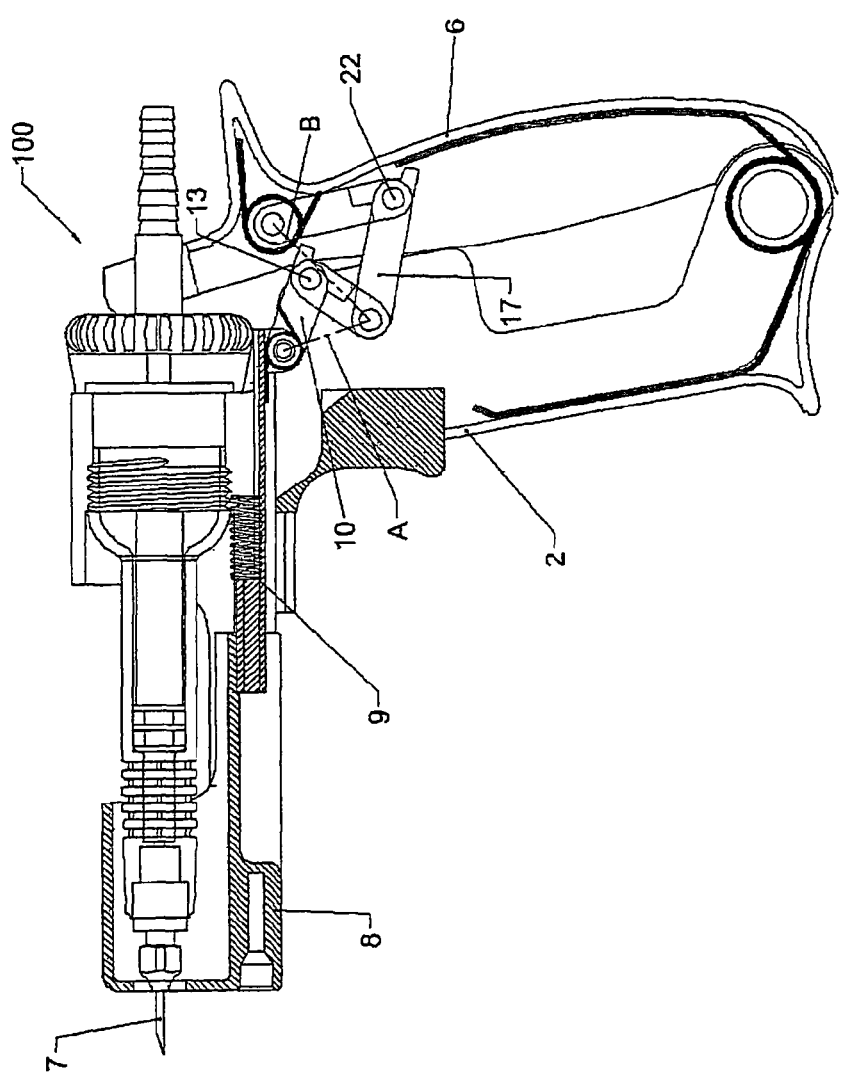
FIG. 4 Is a diagrammatic cross-section side view of the injector of FIG. 1 with both linkages in their collapsed positions, and the handles moved together.

A needle shroud 8 is connected to the body 1 so as to be slideable between the extended position shown in FIG. 1, and the retracted position shown in FIGS. 3 and 4. The needle shroud 8 is preferably biased towards the extended position by a suitable biasing means such as a spring 9 positioned between the needle shroud 8 and the body 1.

In order to reduce the risk of a user accidentally injuring themselves on the needle 7, a mechanism is provided to lock the needle shroud 8 in the extended position when the injector 100 is not in use.

A linkage 10 is rotatably connected to the needle shroud 8 at a first end 11 and to the first handle 2 at a second end 12. The linkage 10 is provided with a hinge 13 between the first and second ends which divides the linkage into a first segment 10a connected to the shroud 8 and a second segment 10b connected to the first handle 2.

With the needle shroud 8 in the extended position, a biasing means such as a torsion spring 14 biases the linkage 10 towards an over-centre locked position, as illustrated in FIG. 1. Any suitable means of locking the linkage when it is in this position may be used, but in a preferred embodiment the first segment 10a of the linkage 10 is provided with a stop portion 15, best seen in FIG. 2. The stop portion 15 engages a portion of the second segment 10b and prevents the hinge 13 from rotating so as to move the hinge 13 any further away from a notional axis A which extends between the centres of the rotatable connections at the first and second ends of the linkage 10. With the linkage 10 in the over-centre locked position the linkage 10 acts as a substantially rigid strut when subject to a force aligned with the notional axis A. The linkage 10 therefore prevents the needle shroud 8 from moving away from its extended position when in the over-centre locked position.

Figure 2:
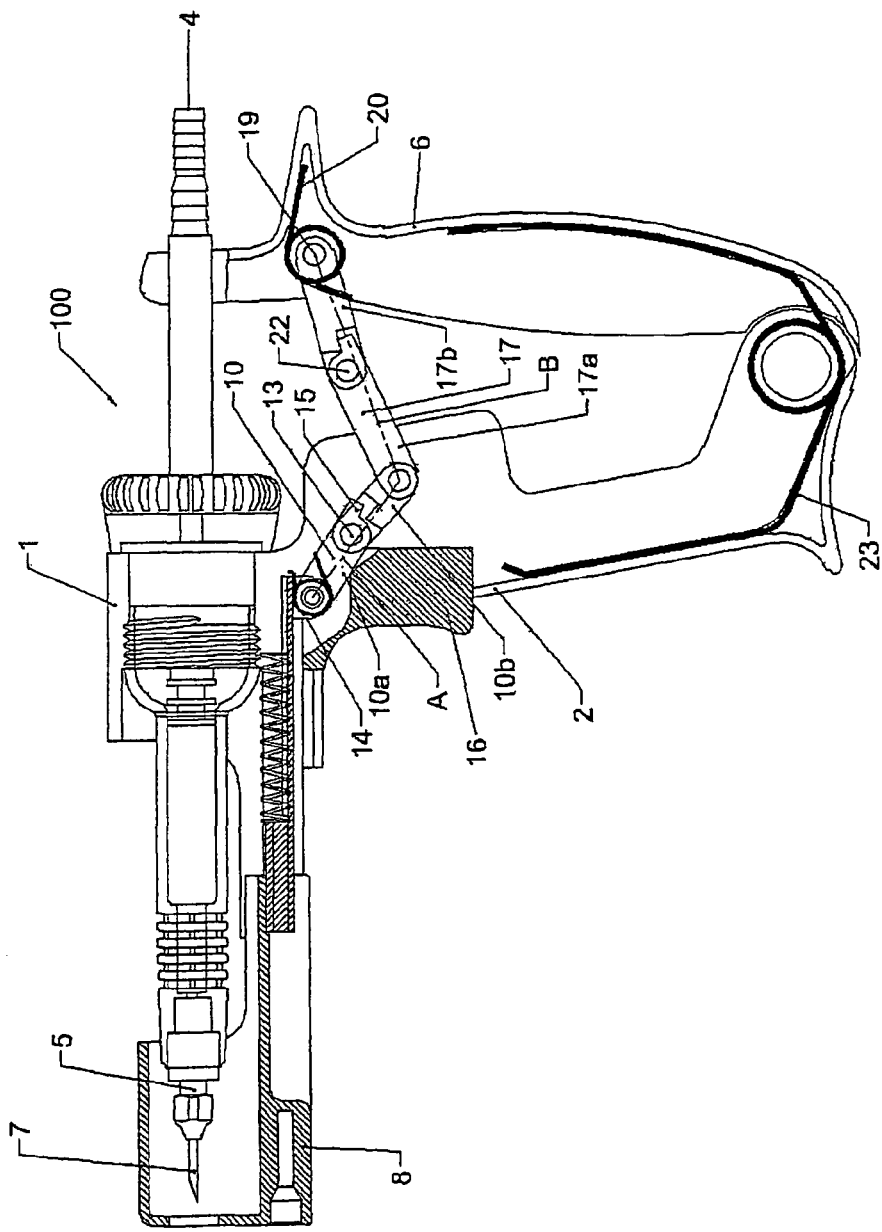
FIG. 2 Is a diagrammatic cross-section side view of the injector of FIG. 1, with the first linkage moved away from the over-centre locked position.

When the user requires the needle shroud 8 to be moved to the retracted position, a linkage unlocking means moves the linkage 10 against the action of the biasing means 14 so that the hinge 13 is on the opposite side of the notional axis A, as shown in FIG. 2. In a preferred embodiment the linkage unlocking means is a trigger 16 which is slideably connected to the first handle 2 and is positioned so as to move into engagement with the linkage 10 when operated by the user, thereby moving the hinge 13 away from the locked position. However, other suitable means of moving the linkage 10 away from the over-centre locked position will be apparent to those skilled in the art.

With the linkage 10 in the position shown in FIG. 2 the needle shroud 8 can be retracted to the position shown in FIG. 3, for example as the needle 7 is inserted into the subject animal.

Referring next to FIGS. 1 and 2, in a preferred embodiment a second hinged linkage 17 is provided between the first handle 2 and second handle 6. The second linkage 17 is rotatably connected at a first end 18 to the first handle 2 and at a second, opposite end 19 to the second handle 6.

The second linkage 17 is biased towards the over-centre locked position shown in FIGS. 1 and 2 by a suitable biasing means such as a torsion spring 20. A first segment 17a of the second linkage 17 is provided with a stop portion 21 which engages a suitable portion of a second segment 17b of the linkage 17, and prevents the hinge 22 from rotating so as to move the hinge 22 any further away from a notional axis B which extends between the centres of the rotatable connections at the first and second ends of the linkage 17. With the second linkage 17 in the over-centre locked position shown in FIGS. 1 and 2 the second linkage 17 is substantially rigid to forces aligned with axis B, and the first handle 2 and second handle 6 cannot be moved together. In this way the chances of accidental dispensing of the remedy are greatly reduced.

In order to unlock the handles 2, 6, the needle shroud 8 must be moved to the fully retracted position shown in FIG. 3. When the needle shroud 8 reaches the fully retracted position a second linkage unlocking portion of the first linkage 10, for example the stop portion 15, engages the second linkage 17 and moves it from the over-centre locked position shown in FIGS. 1 and 2, to the unlocked position shown in FIG. 3.

The first linkage 10 and second linkage 17 may have a pivot axis in common, as seen in the figures. This is not essential, but it does assist in positioning the linkages 10, 17 so that the first linkage 10 can be used to unlock the second linkage 17 when the first linkage 10 moves to the collapsed position.

With the second linkage 17 in the unlocked position the handles 2, 6 can be moved together to the position shown in FIG. 4, thereby delivering a dose of the remedy. A dosage control means may be provided to allow adjustment of the dose delivered. A suitable dosage control means is described in the applicant's New Zealand patent No. 521084, the contents of which are herein included by reference.

Once the dose or remedy has been delivered, the needle 7 is withdrawn from the animal and the handles 2, 6 are allowed to move apart under the action of a suitable biasing means such as a torsion spring 23, thereby drawing a new dose of the remedy from a suitable source through the inlet 4 and into the barrel 3. Biasing means 9 move the needle shroud 8 back to the extended position, and biasing means 14 and 20 move the linkages 10, 17 back to their over-centre locked positions. The injector 100 is therefore reset and ready to dispense a further dose.

In some embodiments the over-centre action of the linkage 17 may mean that the linkage 17 determines the position of the plunger when in the reset position, rather than the plunger returning to a hard stop. This may lead to small deviations in the dose delivered by the applicator. To prevent this, in a preferred embodiment the connection between the end 19 of the second linkage 17 and the second handle 6 may allow a small amount of relative movement. In some embodiments an additional linkage (not shown) may be provided between the end 19 and the second handle 6 to allow for this movement.

A more preferred method of allowing relative movement is described with reference to the preferred embodiment of the first and second linkages shown in FIG. 5, with similar reference numerals indicating similar features as in the other figures. In this embodiment the end 19 of the second linkage 17 is provided with an elongate or slotted aperture 26 within which a pin 27 is provided. The pin 27 is connected to the second handle. The elongate or slotted aperture 26 allows a small amount of sliding movement between handle and the second linkage 17 in addition to allowing rotational movement. Other variations of this system will be apparent to those skilled in the art. For example the second linkage 17 may be provided with projecting pins or similar (not shown) which engage with slots provided in the second handle. In some embodiments a similar system may be used at the opposite end of the second linkage. In other embodiments the aperture may simply be oversized relative to the pin, rather than slotted.

Figure 5:
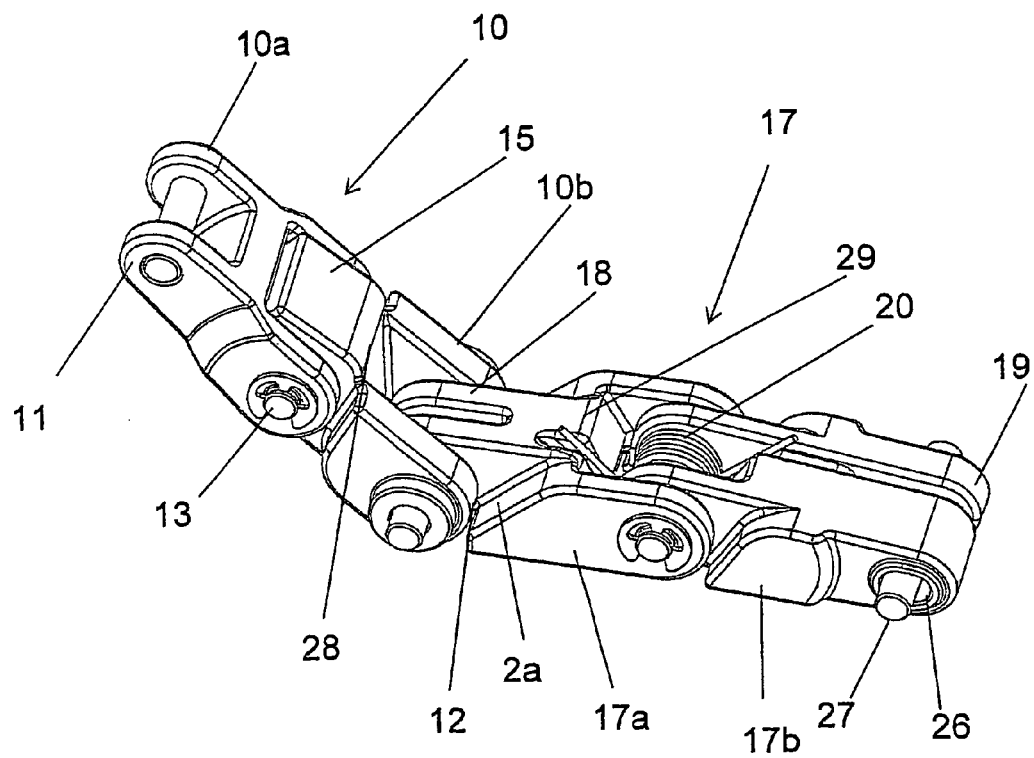
FIG. 5 Is a perspective view of a more preferred embodiment of the first and second hinged linkages, both in an over-centre locked position.

In the embodiment of the linkages shown in FIG. 5, the stop portion 15 is connected to the second segment 10b of the first linkage 10, rather than to the first segment 10a as shown in the embodiment shown in FIGS. 1-4. In the embodiment shown in FIG. 5, the second segment 10b of the first linkage is provided with means to unlock the second segment which includes at least one abutment portion 28 which abuts an abutment portion 29 provided on the first segment 17a of the second linkage 17 when the first linkage 10 is collapsed. This abutment causes the second linkage 17 to move away from its over-centre locked position to its collapsed position.

While the present invention has been described with reference to an embodiment in which the dose is applied by squeezing the handles 2, 6 together to manually actuate a plunger, those skilled in the art will appreciate that in some other embodiments of the invention the injector may be adapted so that the plunger is actuated by an alternative means, such as a pressurised gas. In a still further alternative embodiment the remedy may be supplied to the inlet under pressure and the movement of the handles may actuate a valve which allows the remedy to flow from the inlet to the outlet. Suitable means for controlling the volume of remedy delivered may be required with this embodiment.

Those skilled in the art will appreciate that in an alternative embodiment of the injector (not shown) the first linkage 10 may be omitted, and some other means of locking the needle shroud may be provided, if required. In these embodiments the second linkage 17 may be unlocked by some other suitable means such as, for example, a trigger. This method of locking the flow control means may also be used with dispensing means other than injectors, for example pour on applicators and the like.

In a further embodiment (not shown) the applicator may be provided with the first linkage 10, but the second linkage 17 may be omitted. This configuration may be useful where the applicator has a particularly delicate application means, such as a needle or a delicate nozzle, but where the remedy being dispensed is not harmful to humans.

Figure 6:
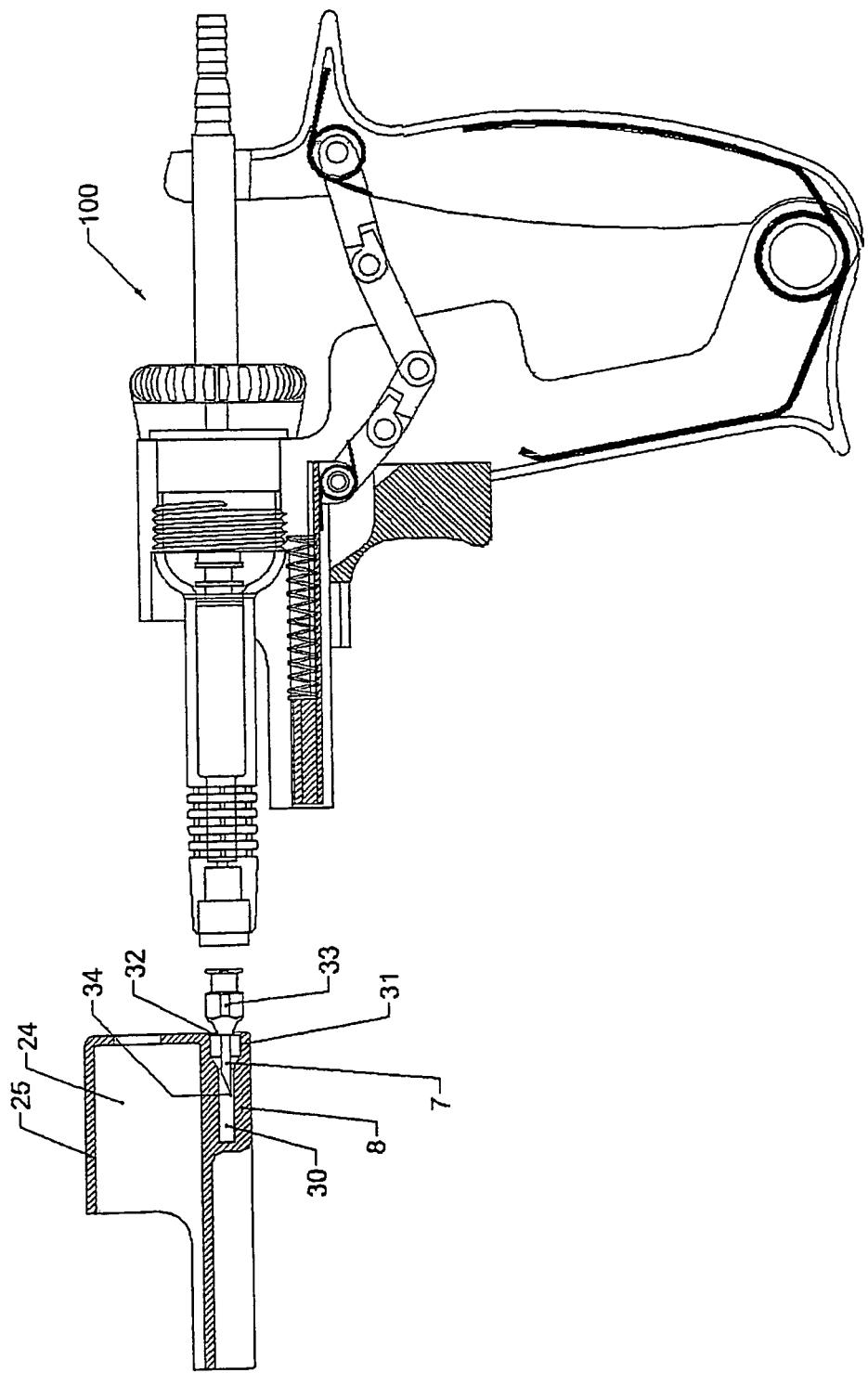
FIG. 6 Is an exploded diagrammatic cross-section side view of the injector of FIG. 1 showing the needle shroud component in position for use in removing the needle from the injector.

Referring next to FIGS. 1, 1a and in particular FIG. 6, in a preferred embodiment the needle shroud 8 is provided with means for assisting with the removal of the needle 7.

In this embodiment the needle shroud 8 is detachable from the body of the injector 100. In addition to the aperture 24 in the body 25 of the shroud 8, through which the needle 7 can extend when the shroud 8 is attached to the injector 100, the shroud 8 is also provided with a cavity 30 shaped and dimensioned to receive the needle 7 when the user wishes to remove the needle 7 from the injector 100.

The cavity 30 has a formation 31, best seen in FIG. 1A, preferably provided at or adjacent the mouth 32 of the cavity 30, which is shaped and dimensioned to engage a complementary formation 33 of the needle 7. In a preferred embodiment the formation may be a square drive formation as shown in FIG. 1A.

The provision of the cavity 30 and formation 31 allows the point of the needle 7 to covered when the needle 7 is removed from the injector 100. The cavity mouth 32 may be provided at either end of the body of the shroud 8. In some embodiments (not shown) the cavity may extend through the body of the shroud 8, but it is preferred that the cavity is shaped so that the needle point 34 can not protrude from the cavity 30.

Some needles for use with such injectors are supplied in a two-part plastic sheath (not shown). One part of the sheath has a socket for the needle hub and the needle sits into the socket with the needle cannula protruding into the sheath so that the sharp end of needle is protected. The sheath can be held and used as a tool to attach the needle to the luer lock of an injector.

The aperture 24 in the needle shroud 8 of the present invention is preferably dimensioned to allow such a sheath to be inserted through the front of the shroud so that the needles can be fitted and removed without having to remove the shroud 8 from the injector 100.

Those skilled in the art will appreciate that the needle shroud 8 described above may be used with other injectors of the prior art, but when used in association with the injector 100 described above there is provided an injector which allows a user to inject a remedy into an animal, and to change a needle of the injector, with minimal risk of needle stick or of accidental delivery of the remedy into the user.

While the applicator shown in the figures is adapted for use with a remote supply of remedy, for example from a backpack, those skilled in the art will appreciate that the invention may also be used with applicators which are provided with a bottle mount on which a bottle containing the remedy may be mounted. Still other embodiments may be loaded with a cartridge or vial.

Where in the foregoing description, reference has been made to specific components or integers of the invention having known equivalents, then such equivalents are herein incorporated as if individually set forth.

Although this invention has been described by way of example and with reference to possible embodiments thereof, it is to be understood that modifications or improvements may be made thereto without departing from the spirit or scope of the appended claims.

The invention claimed is:

1. An applicator comprising:
   an inlet for receiving a fluid to be dispensed;
   an outlet for dispensing the fluid to be dispensed;
   flow control means for controlling flow from the inlet to the outlet, the flow control means including a first member and a second member, the arrangement being such that relative movement of the first member towards the second member causes fluid to flow from the outlet;
   a hinged linkage having a first end rotatably engaged with the first member, a second end rotatably engaged with the second member, and a hinge intermediate the first and second ends, the linkage being moveable between a collapsed position wherein the hinge is on a first side of an imaginary axis extending between the first and second ends, and an over-centre locked position wherein the hinge is on an opposite side of the imaginary axis between the first and second ends and the hinged linkage prevents relative movement of the first member towards the second member; and linkage unlocking means operable to move the hinge from the over-centre locked position to the first side of the imaginary axis between said first and second ends, so that the hinged linkage can be moved to the collapsed position as the first and second members are moved together.

2. The applicator of claim 1, wherein the linkage is biased towards the over-centre locked position.

3. The applicator of claim 1, wherein the linkage unlocking means includes a trigger.

4. The applicator of claim 1, wherein at least one of the connections between the ends of the hinged linkage and the first and second members allows relative movement between the linkage and the respective member in addition to the rotational movement.

5. The applicator of claim 4, wherein the relative movement includes slideable movement between the respective member and the end of the hinged linkage.

6. The applicator of claim 4, wherein at least one of the connections between the ends of the hinged linkage and the first and second members includes a pin slideably engaged with a slot.

7. The applicator of claim 1, wherein the applicator is suitable for applying an animal remedy to an animal.

8. The applicator of claim 1, wherein the first and second members are handles.

9. The applicator of claim 1, wherein the applicator is an injector.

10. An applicator comprising:
a body provided with a first handle;
an inlet for receiving a remedy to be dispensed;
an outlet for dispensing the remedy, the outlet provided with application means connection means for connecting an application means to the outlet;
flow control means for controlling flow of the remedy from the inlet to the outlet;
a shroud connected to the body and moveable between an extended position wherein the shroud covers an application means attached in use to the application means connection means, and a retracted position wherein a required length of the application means protrudes from the shroud;
a first hinged linkage having a first end rotatably engaged with the shroud, a second end rotatably engaged with the first handle, and a hinge intermediate the first and second ends, the first hinged linkage being moveable between a collapsed position wherein the hinge is on a first side of an imaginary axis extending between the first and second ends, and an over-centre locked position wherein the hinge is on an opposite side of the imaginary axis between the first and second ends, the arrangement being such that the hinged linkage prevents the shroud froth moving from the extended position when in the over-centre locked position;

biasing means to bias the first hinged linkage towards the over-centre locked position; and linkage unlocking means operable to move the hinge from the over-centre locked position to the first side of the imaginary axis between the first and second ends, so that the linkage can be moved to the collapsed position as the shroud is moved to the retracted position.

11. The applicator of claim 10, wherein the flow control means includes a second handle, and wherein relative movement of the second handle towards the first handle causes the remedy to flow from the outlet, and the applicator includes a second hinged linkage having a first end rotatably engaged with the first handle, a second end rotatably engaged with the second handle, and a hinge intermediate the first and second ends, the second hinged linkage moveable between a collapsed position wherein the hinge is on a first side of an imaginary axis extending between first and second ends, and an over-centre locked position wherein the hinge is on an opposite side of the imaginary axis between the first and second ends and the second hinged linkage prevents relative movement of the second handle towards the first handle, the arrangement being such that movement of the first hinged linkage to the collapsed position causes the hinge of the second hinged linkage to move from the over-centre locked position to the first side of the imaginary axis between the first and second ends of the second hinged linkage, so that the second hinged linkage can be moved to the collapsed position as the first and second handles are moved together.

12. The applicator of claim 11, wherein at least one of the connections between the ends of the second hinged linkage and the handles allows relative movement between the linkage and the respective handle in addition to the rotational movement.

13. The applicator of claim 12, wherein the relative movement includes slideable movement between the end of the second hinged linkage and the respective handle.

14. The applicator of claim 11, wherein at least one of the connections between the ends of the second hinged linkage and the handles includes a pin slideably engaged with a slot.

15. The applicator of claim 10, wherein the body is connected to a first end of the first handle.

16. The applicator of claim 15, wherein the second handle is rotatably connected to the first handle at a distal end to the body.

17. The applicator of claim 10, wherein the shroud is biased towards the extended position.

18. The applicator of claim 10, wherein the applicator is an injector and the application means is a needle.

* * * * *

UNITED STATES PATENT AND TRADEMARK OFFICE
CERTIFICATE OF CORRECTION

PATENT NO. : 8,641,682 B2  
APPLICATION NO. : 12/451566  
DATED : February 4, 2014  
INVENTOR(S) : Walker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 964 days.

Signed and Sealed this

Twenty-second Day of September, 2015

Michelle K. Lee
*Director of the United States Patent and Trademark Office*